(12) United States Patent
Levenson et al.

(10) Patent No.: US 8,497,066 B2
(45) Date of Patent: Jul. 30, 2013

(54) DNA METHYLATION BASED TEST FOR MONITORING EFFICACY OF TREATMENT

(75) Inventors: Victor Levenson, Chicago, IL (US); Anatoliy Melnikov, Glenview, IL (US); Roumen Balabanov, Chicago, IL (US); Dusan Stefoski, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 519 days.

(21) Appl. No.: 12/631,622

(22) Filed: Dec. 4, 2009

(65) Prior Publication Data

US 2010/0143929 A1 Jun. 10, 2010

Related U.S. Application Data

(60) Provisional application No. 61/119,989, filed on Dec. 4, 2008.

(51) Int. Cl.
*C12Q 1/68* (2006.01)

(52) U.S. Cl.
USPC ......................................................... 435/6.1

(58) Field of Classification Search
None
See application file for complete search history.

(56) References Cited

U.S. PATENT DOCUMENTS

| | | | | |
|---|---|---|---|---|
| 6,043,088 | A * | 3/2000 | Bookstein et al. | 435/366 |
| 6,331,393 | B1 * | 12/2001 | Laird et al. | 435/6.12 |
| 2003/0186277 | A1 * | 10/2003 | Olek et al. | 435/6 |
| 2003/0232351 | A1 * | 12/2003 | Feinberg | 435/6 |
| 2004/0137474 | A1 | 7/2004 | Levenson et al. | |
| 2005/0021240 | A1 | 1/2005 | Berlin et al. | |
| 2008/0261217 | A1 | 10/2008 | Melnikov et al. | |

FOREIGN PATENT DOCUMENTS

WO WO 2005/019477 3/2005

OTHER PUBLICATIONS

Anker et al. (Clin Chim Acta. Nov. 2001;313(1-2):143-6).*
Davidovich et al, "Overexpression of DcR1 and survivin in genetically modified cells with pleitropic drug resistance," *Cancer Letters*, 211: 189-197 (2004).
Levenson et al, "DNA methylation biomarkers of cancer: moving towards clinical application," *Pharmacogenomics*, 5(6): 1-9 (2004).
Melnikov et al, "MSRE-PCR for analysis of gene-specific DNA methylation," *Nucleic Acids Research*, 33(10): e93 (2005).
Melnikov et al, "Array-based multiplex analysis of DNA methylation in breast cancer tissues," *Jrnl. Molecular Diag.*, 10(1): 93-101 (2008).
International Search Report issued in application No. PCT/US09/66855 (2010).
Bhandare et al, "Isolation of highly purified DNA from low-abundance archived and stained cytological specimens," *Clinica Chimica Acta*, 367: 211-213 (2006).
Levenson et al., "Biomarkers for early detection of breast cancer: What, when, and where?," *Biochimica and Biophysica Acta*, 1770: 847-856 (2007).
Liggett et al., "Differential methylation of cell-free circulating DNA among patients with pancreatic cancer versus chronic pancreatitis," *Cancer*, 1-18 (2010).
Liggett et al., "Methylation patterns of cell-free plasma DNA in relapsing-remitting multiple sclerosis," *Journal of the Neurological Sciences*, 290: 16-21 (2010).
Melnikov et al., "Array-Based Multiplex Analysis of DNA Methylation in Breast Cancer Tissues," *Journal of Molecular Diagnostics*, 10(1): 93-101 (2008).
Melnikov et al., "Differential Methylation Profile of Ovarian Cancer in Tissues and Plasma," *Journal of the Molecular Diagnostics*, 11(1): 60-65 (2009).
Melnikov et al., "Methylation Profile of Circulating Plasma DNA in Patients With Pancreatic Cancer," *Journal of Surgical Oncology*, 99(2): 119-122 (2009).
Sepulveda et al., "CpG Methylation Analysis—Current Status of Clinical Assays and Potential Applications in Molecular Diagnostics," *Journal of Molecular Diagnostics*, 11(4): 266-278 (2009).

* cited by examiner

*Primary Examiner* — Christopher M. Babic
(74) *Attorney, Agent, or Firm* — Barnes & Thornburg LLP; Alice O. Martin (57) ABSTRACT

A DNA methylation-based test for efficiency of treatments is based on a plurality of genes. The test is suitable for monitoring treatment of subjects with neurological diseases, e.g., multiple sclerosis (MS); with cancer, e.g., breast and ovarian cancer, and with other diseases for which methylation of biomarkers differs in the diseased compared to the non-diseased state.

8 Claims, 4 Drawing Sheets

DNA METHYLATION BASED TEST FOR MONITORING EFFICACY OF TREATMENT

This patent application claims priority to copending U.S. Ser. No. 61/119,989 filed Dec. 4, 2008.

This invention was made with government support under Grant No. R 21 NS060311 awarded by NIH, NINDS. The government has certain rights in the invention.

BACKGROUND

A DNA methylation-based test for efficiency of treatment is based on a plurality of genes. The test is suitable for monitoring treatment of subjects with neurological diseases, e.g., multiple sclerosis (MS); with cancer, e.g., ovarian and breast cancers, and with other diseases for which methylation of biomarkers differs in the diseased compared to the non-diseased state. The test is also suitable to differentiate non-affected from asymptomatic but affected and different states of diseases.

Several diagnostic tests are used to rule out or confirm cancer. For many cancers, the most definitive way to do this is to obtain a sample of the suspect tissue by biopsy followed by pathological analysis. However, biopsies are invasive, unpleasant procedures with their own associated risks, such as pain, bleeding, infection, and tissue or organ damage. In addition, if a biopsy does not result in an accurate or large enough sample, a false negative or misdiagnosis can result, often required that the biopsy be repeated. Monitoring treatment effects is also difficult.

Abnormal DNA methylation of cancer cells is reported. Tumor-specific changes in DNA methylation have been observed in many different malignancies and are frequently described as global hypomethylation combined with local hypermethylation. Global hypomethylation is linked to genomic instability of a tumor, whereas hypermethylation of specific genes correlates with their silencing and can induce point mutations owing to spontaneous deamination of 5me-C (transversion C→T). Silencing of a tumor suppressor gene can lead to enhanced transformation and increased tumor growth through disruption of the normal regulatory mechanisms of the affected cell.

Breast cancer, which is treatable by surgery, radiation therapy, chemotherapy, and hormonal therapy, is most often curable when detected in early stages. Mammography is the most important screening modality for the early detection of breast cancer. Breast cancer is classified into a variety of sub-types, but only a few of these affect prognosis or selection of therapy. Patient management following initial suspicion of breast cancer generally includes confirmation of the diagnosis, evaluation of stage of disease, and selection of therapy. Diagnosis may be confirmed by aspiration cytology, core needle biopsy with a stereotactic or ultrasound technique for nonpalpable lesions, or incisional or excisional biopsy. At the time the tumor tissue is surgically removed, part of it is processed for determination of Estrogen Receptor (ER) and Progesterone Receptor (PR) levels.

Prognosis and selection of therapy are influenced by the age of the patient, stage of the disease, pathologic characteristics of the primary tumor including the presence of tumor necrosis, estrogen-receptor (ER) and progesterone-receptor (PR) levels in the tumor tissue, and measures of proliferative capacity, as well as by menopausal status and general health. Overweight patients may have a poorer prognosis. Prognosis may also vary by race, with blacks, and to a lesser extent Hispanics, having a poorer prognosis than whites.

Three major treatments for breast cancer are surgery, radiation, and drug therapy. No treatment fits every patient, and often two or more treatments are required. The choice is determined by many factors, including the age of the patient and her menopausal status, the type of cancer (e.g., ductal vs. lobular), its stage, whether the tumor is hormone-receptive or not, and its level of invasiveness.

Breast cancer treatments are defined as local or systemic. Surgery and radiation are considered local therapies because they directly treat the tumor, breast, lymph nodes, or other specific regions. Drug treatment is called systemic therapy, because its effects are widespread. They may be used separately or, most often, in different combinations.

Ovarian cancer is the eighth most common cause of cancer mortality in women. It is diagnosed in more than 20,000 women in the USA each year and approximately 15,000 women die of the disease annually. Early detection and diagnosis of ovarian cancer has the potential to reduce cancer-related mortality and improve quality of life. Unfortunately, early stages of ovarian cancer are mostly asymptomatic, so its early detection has to rely on screening of ostensibly healthy population. This brings very high demands on the specificity and sensitivity of the assay, on the accessibility of patients' specimens, and on the overall cost of the procedure. In addition, compliance issues have to be considered—a painful, uncomfortable, or embarrassing procedure may be unpopular even if all the other components are in place. Tumor-specific DNA is present in the bloodstream and its methylation reflects the methylation in the primary tumor, while changes in methylation are linked to changes in gene expression and thus reflect long-term functional status of the tumor. Existing techniques are limited to imaging modalities such as transvaginal sonography (TVS) and blood-based biomarkers.

Other diseases for which methylation of DNA offers prognosis and treatment monitoring include neuroinflammatory demyelinating diseases, defined as any disease of the nervous system in which the myelin sheath of neurons is damaged and inflammation occurs, thereby impairing the conduction of signals in the affected nerves, causing impairment in sensation, movement, cognition, or other functions depending on which nerves are involved. The term describes the effect of the diseases, rather than their causes. Some demyelinating diseases are caused by infectious agents, some by autoimmune reactions, and some by unknown factors. Organo-phosphates, a class of chemicals that are the active ingredients in commercial insecticides such as sheep dip, weed-killers, and flea treatment preparations for pets and the like will also demyelinate nerves. Demyelinating diseases include multiple sclerosis (MS), acute disseminated encephalomyelitis, optic neuritis, transverse myelitis, Devic's disease, Guillain-Barre syndrome, chromic inflammatory demyelinating polyneuritis and progressive multifocal leukoencephalopathy (PML).

Multiple sclerosis (MS) is an example of a disease that is difficult to diagnose in its early stages. In fact, definite diagnosis of MS cannot be made until there is evidence of at least two anatomically separate demyelinating events occurring at least thirty days apart. The McDonald criteria represent international efforts to standardize the diagnosis of MS using clinical data, laboratory data, and radiologic data. Furthermore, a number of diseases can mimic the clinical presentation of MS, which requires an extensive prediagnosting evaluation.

There is an unmet need for accessible, inexpensive, and objective biomarkers for multiple sclerosis (MS) that can be used as a metric for the disease. Such biomarkers should distinguish MS after the initial clinically isolated syndrome and before new lesions develop in the CNS. They should also identify imminent exacerbations before clinical symptoms develop and additional CNS damage has already occurred. Ideally, such biomarkers should also identify exacerbations that do not produce clinical symptoms but nonetheless create CNS damage as evidenced by gadolinium-enhanced lesions.

Figure 1:
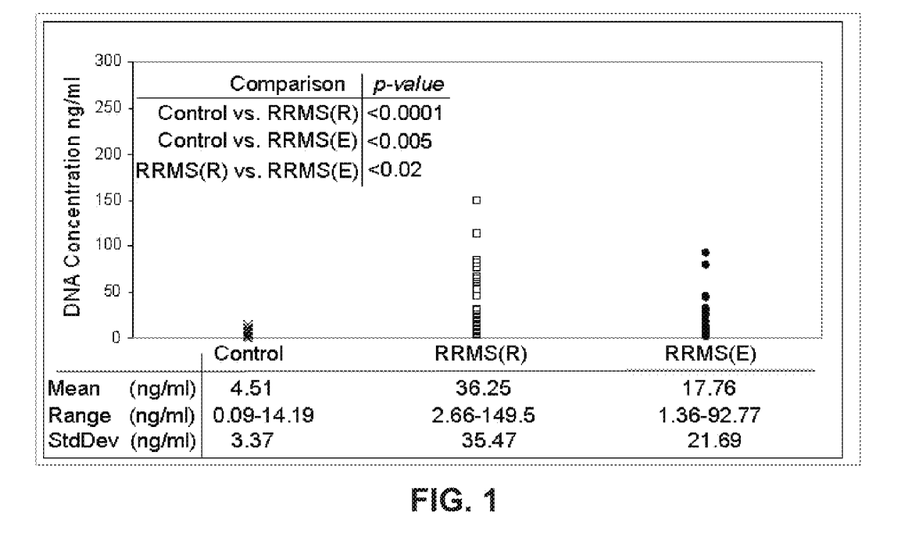
FIG. 1 is a concentration of cfpDNA and is higher in MS patients compared to healthy controls.

Concentration of cfpDNA in blood of patients with RRMS is higher than in healthy controls (FIG. 1) and has specific methylation patterns, which can distinguish RRMS patients from healthy individuals, can separate patients who are undergoing clinical exacerbation [RRMS(E)] from those in remission [RRMS(R); Table 5 and distinguish patients treated with disease-modifying agents from those who are treatment naïve.

Disease exacerbation is defined, e.g., as presence of new or worsened symptoms and neurologic deficits lasting at least 72 hours.

Six drugs have been approved by the US Food and Drug Administration for treatment of MS as capable of decelerating its activity or progression, or both. All are parenteral, injected subcutaneously, intramuscularly or intravenously. Betaseron®, the first interferon beta (IFN-β) to be approved by the FDA (1993), was shown to reduce inflammation, decrease MS relapse rate, increase time between attacks, decrease the severity of attacks, and decrease the accumulated MS lesions as seen on MRIs of the brain. Betaseron® is administered every other day by subcutaneous injection, and is approved for relapsing forms of MS. Avonex® (IFN β-1a) was the first IFN-β to demonstrate and receive the FDA approval for slowing the rate of progression of disabilities in RR MS. It also decreases relapse rate and the accumulation of MS lesions on brain MRI. It is given as weekly intramuscular injections, and is indicated for the treatment of RRMS. Rebif® (IFN β-1a) although produced similarly to Avonex® by the Chinese hamster ovary cells, its formulation and administration are different to accommodate the thrice weekly subcutaneous route. Rebif® was proven efficacious in reducing the number and severity of relapses, delaying the progression of disabilities, and reducing the number of new and enlarging MS lesions on brain MRIs. It is approved for use in RRMS. Copaxone® (glatiramer acetate) was approved for decreasing the MS exacerbation rate and accumulation and activity of MS lesions on MRIs of the brain, albeit somewhat less than the interferons beta. It is administered daily by subcutaneous injection and is used in RRMS. Tysabri® (natalizumab) is the first monoclonal antibody approved by the FDA as monotherapy for relapsing forms of MS, and has shown efficacy in reducing relapse rates, progression of disabilities, and accumulation of new and active lesions on MRIs of the brain. Although head-to-head trials with IFNs β or glatiramer have not been done to validate comparison statements, numerically and statistically the efficacy of Tysabri® seemingly exceeds theirs, being in the 50% to 70% range clinically. It is administered intravenously once per month. A little over 25,000 MS patients are receiving it since marketing started 2 years ago. Novantrone® (mitoxantrone) is a cytotoxic agent that slows progression of disabilities and reduces the number of MS relapses. It is FDA approved for refractory SP and RR MS, and is recommended for use only over a limited time and in limited doses to avoid the serious adverse cardiac and myeloproliferative effects. It is administered intravenously, usually once every three months for up to two years. In addition, corticosteroids (prednisone, prednisolone, methylprednisolone, and dexamethasone) are used for the treatment of acute exacerbations to shorten their duration and speed up clinical recoveries. Although they have not been proven to alter the frequency of exacerbations or the progression of MS, the optic neuritis treatment trial has demonstrated that a single course of intravenous methylprednisolone (Solu-Medrol®) was capable of reducing the accumulation of new lesions on brain MRIs over two years.

The practical use of medications to treat MS, however, faces important pitfalls. Treatment failure rate differs depending on criteria used to determine success. Their efficacy is usually modest or associated with significant side effects, and a large number of patients either do not respond to or discontinue them. Medication failure is usually determined clinically, after disease worsening, or appearance of new lesions on MRI imaging. Such determination takes significant amount of time (months or years) and sometimes after the appearance of irreversible neurological deficits. The clinical follow up of patients also includes monitoring of side effects that can range from flu-like symptoms to liver failure and death. At this point there are no means to predict patients' response to therapy and the potential scope of side effects. Thus, there is an unmeet need for objective laboratory-based biomarkers for treatment efficacy or related side effects that can be followed, and acted upon prior to the appearance of clinical symptoms.

Methylation-sensitive restriction enzyme digestion PCR (MSRE-PCR), can be used for rapid detection of DNA methylation in multiple fragments simultaneously. This procedure is based on extensive digestion of genomic DNA with methylation-sensitive restriction enzymes (MSRE) followed by multiplexed PCR amplification of user-defined genes using gene-specific primers. Although elimination of unmethylated fragments from the pool of potential PCR templates by MSRE digestion has been attempted previously, the requirements for high specificity and sensitivity of the assay present substantial problems that have been resolved in MSRE-PCR, which allows analysis of DNA methylation in a genomic equivalent of seven cells and can reliably detect methylation present in <2% of the sample.

SUMMARY

Methods and compositions are provided for reliable diagnostic (e.g., detection) and prognostic methods to identify and monitor response to treatment of neuroinflammatory demyelinating diseases and cancers.

Simultaneous assessment of DNA methylation in multiple loci in each patient sample results in the most informative loci being analyzed together as a composite biomarker.

Genome-wide methylation testing is done in CpG island-containing promoters. Assays using more than 12,000 genes are provided in an embodiment.

Changes in methylation profile from healthy to disease state can be used for disease detection; in a similar manner persistence of abnormal pre-treatment profiles may delineate resistance to treatment, while re-appearance of the pathological process may cause re-appearance of the corresponding profile. In this respect, methylation profiles can be used for disease monitoring on different levels, from treatment effect to recurrence of the disease. Deviations of methylation profiles from the normal non-diseased state are used to detect asymptomatic subjects, and to classify disease states.

Suitable diseases for the methods disclosed herein include neuroinflammatory demyelinating diseases, e.g., Multiple Sclerosis (MS), and cancer, e.g., ovarian and breast cancers. An example of a treatment for MS is Tysabri®, for breast cancer, tamoxifen.

Given that DNA methylation is a specific chemical modification of one of the most stable biological macromolecules, the DNA methylation status of a selected gene or plurality of genes is an attractive biomarker to use for early diagnosis, outcome prediction and therapy adjustments.

Monitoring patients (subjects) for responses to treatment for diseases that can be detected and monitored by DNA methylation patterns, is needed so treatment regimens are optimized, i.e., treatment does not continue if ineffective or appears completed. Pre-screening patients for response to therapies is also helpful.

Compositions and methods for monitoring treatment of diseases are described. Three outcomes can be foreseen; no change in treated versus untreated patient status (ineffective therapy); change to a healthy profile, and change to a different profile. The latter outcome defines drug effects and may correlate with curative action.

A composite biomarker identifies changes in DNA methylation of treated patients. A composite biomarker is a biomarker that consists of multiple elements that have to be evaluated as a combination to achieve required precision. Each component by itself has only a limited value. It can be used to monitor efficacy of treatment and can be used as "a Surrogate Biomarker." A Surrogate Biomarker is a biomarker that substitutes for a clinical endpoint. A Surrogate Biomarker is expected to predict clinical benefit (or harm or lack of benefit or harm) based on epidemiologic, therapeutic, pathophysiologic, or other scientific evidence. The inventors are not aware that the composite biomarkers described herein has been used to monitor treatment in patients, or that described changes in methylation profile have been reported. No analogous technologies are reported for treatment monitoring.

For example, a composite biomarker including DNA methylation identifies efficacy of a treatment for a disease by:

(a) determining DNA methylation status of genes in a sample of DNA from healthy (non-diseased) mammals (controls), or from diseased mammals without progression;

(b) determining DNA methylation of genes in a sample of DNA from mammals with progressive disease;

(c) determining genes differentially methylated between (a) and (b);

(d) administering the treatment to mammals with the progressive disease;

(e) comparing DNA methylation between the healthy controls, or diseased mammals without progression, and the mammals with progressive disease before and after the treatment; and (f) inferring that the treatment is effective if methylation status of treated mammals moves toward values in healthy controls or untreated diseased mammals without progression, and/or away from values in diseased mammals with progressive disease.

A method to determine efficacy of a treatment for a disease in a mammal includes:

(a) identifying a plurality of genes that are differentially methylated in mammals that do not have the disease (controls) compared to untreated mammals with the disease; controls should be matched, e.g., for age, sex and race;

(b) comparing methylation profiles of a biological sample, e.g., cell-free circulating DNA from plasma, of the mammal being treated, to methylation profiles of those who are not treated; and (c) inferring from the comparison in (b) that the treatment is effective if the methylated profiles are more similar to profiles of mammals who do not have the disease, than to the methylation profiles for untreated diseased mammals.

Additional informative elements, e.g., proteins, cytokines, autoantibodies, microRNA, metabolites and the like, may be incorporated into the biomarkers disclosed herein.

In an embodiment, a concurrent analysis of DNA methylation in multiple genes using cell-free circulating DNA from plasma of MS patients identified a set of genes that were differentially methylated in healthy controls and patients treated e.g., with anti-MS drugs. A set of the most differentially methylated genes provided sensitivity of 96% and specificity of 81% for detection of response to MS treatment.

Thus, molecular differences in tumors reflect differences in gene expression, which are in turn reflected in differential DNA methylation, mostly in CpG islands of gene promoters. In case of ovarian cancer such differences have already been noted but attempts to develop a marker have met with limited success due to the lack of a robust analytical platform. A new platform (MethDet-12k), was developed as the next generation of the prototype platform MethDet-56. Biomarkers for ovarian cancer and breast cancer, are developed.

DETAILED DESCRIPTION

DNA methylation is one of the mechanisms for regulating gene expression. In abnormal cells, anomalous hypermethylation correlates with inactivation of e.g., tumor suppressors, while irregular hypomethylation correlates with activation of oncogenes. Changes of methylation changes susceptibility of genomic DNA to methylation-sensitive restriction enzymes, such that only hypomethylated DNA can be destroyed by such enzymes. Digestion with methylation-sensitive restriction enzymes leads to destruction of the integrity of the genomic DNA, such that it can no longer serve as a template for polymerase chain reaction (PCR) amplification. In contrast, hypermethylated DNA is insensitive to methylation-sensitive restriction enzymes and can be amplified. The comparison of amplification products of undigested (control) and digested (target) DNA identifies hypo- and hypermethylated fragments. The method includes (1) successful digestion of susceptible DNA with methylation-sensitive restriction enzymes; (2) amplification of selected fragments in control and test samples; (3) competitive hybridization of amplified products to a microarray (e.g., allowing for high-throughput analysis); and (4) scoring the results. Disease specific cell-free DNA is present in blood, is isolated from plasma, and serves as a genomic DNA for generation of the methylation profiles that are then correlated with treatment effects. Other biological samples are also suitable.

Existing technologies do not allow for high-throughput methylation analysis in multiple genes and require substantially larger amounts of DNA (10-100 times more) for analysis, and are therefore unable to produce comprehensive methylation profiles required for diagnosis or monitoring.

Simultaneous analysis of DNA methylation in many genes allows for a methylation profile that is correlated to a particular disease, e.g., a neuroinflammatory demyelinating disease, such as multiple sclerosis, or a cancer such as ovarian and breast cancer. A composite biomarker is a biomarker that consists of multiple elements that have to be evaluated as a combination to achieve a higher level of precision than can be achieved by evaluation of each of the elements separately. In some embodiments, the methylation profile is based on cell free DNA from blood plasma, thereby bypassing painful and invasive sample acquisition such as lumbar puncture to obtain CSF or a breast tissue biopsy. A methylation profile can contain any number of analyzed genes as long as the combination of genes tested is diagnostically relevant to the particular disease or other purposes. For example, Table 1 shows a profile of genes differentially methylated ($p<0.01$) in patients with and without MS. The method is useful for adaptation for specific localization of a neuroinflammatory demyelinating disease thereby offering a wide range of diagnostic possibilities.

DNA-Based Biomarkers.

Protein tests are reported for ovarian cancer for example. Accuracy of the test relies on the sensitivity of the assay and that in turn depends on the nature of the analyte. In this respect protein-based assays can be not as sensitive as DNA-based tests—DNA amplification by polymerase chain reaction (PCR) detects a single copy of DNA, which may be difficult to match for protein-based assays.

DNA-based testing does not have to evaluate genetic changes; it can be based on epigenetic modifications of DNA. Methylation of cytosines in cytidine-guanosine dinucleotides (CpG) is the most frequent epigenetic event, and multiple genes are known to be abnormally methylated in ovarian cancer. A test based on this abnormal methylation would have solved the problem of cancer detection if any gene(s) was known to be always methylated in one condition, and unmethylated in others. Unfortunately, such a gene has yet to be found, and the general redundancy of regulatory pathways argues against this possibility. Indeed, there is no single gene consistently methylated even when tumors are compared to healthy tissues, so a single gene-based assay is hardly the answer. This problem can be resolved if many genes are tested in the same clinical sample, so that the probabilities of methylation are combined to increase accuracy of the test. In this regard, the methylation test follows the logic of composite biomarkers, established for protein assays with the added benefit of simplicity provided by PCR-based analysis of DNA methylation without the need for complex techniques such as mass-spectroscopy.

A biological sample is obtained from a subject (e.g., blood, plasma, serum, other bodily fluids (e.g., saliva, urine), tissue, and cytological samples), and includes genomic DNA. The presence or absence of DNA methylation in one or more genes generates a methylation profile for the subject. Comparing the methylation profile to one or more standard methylation profiles, wherein the standard methylation profiles includes methylation profiles of samples that come from subjects known not to have a disease (including prior results from the tested individual prior to a disease state) and methylation profiles of disease from those with samples, and/or methylation profiles of the subject before treatment, allow clinical decisions to be made. Detecting the presence or absence of DNA methylation includes the digestion of the genomic DNA with a methylation-sensitive restriction enzyme followed by amplification of gene-specific DNA fragments, which optionally may include multiplex amplification. Optionally, the amplified DNA may include one or more CpG-containing sequences (or CpG islands) which are not digested by the methylation-sensitive restriction enzyme.

Many of the problems of mRNA arrays to evaluate gene expression (e.g., stability of RNA and quantitation of expression) are overcome by measuring methylation profiles of CpG-containing sequences. Regions of unusually high GC content have been described in many genes and may be referred to as "CpG islands". The cytosine of CpG islands can be modified by methyltransferase to produce a methylated derivative—5-methylcytosine.

Methylation analysis is improved by providing a technique for high throughput analysis without loss in sensitivity. The first phase of the assay involves digestion of genomic DNA with a methylation-sensitive enzyme (e.g., HpaII or Hin6I), which cuts unmethylated sites, for example GCGC, while leaving even hemi-methylated sites intact. Efficiency of this step determines the discriminating power of the approach, since the next procedure—amplification of the CpG island-containing fragments with primers flanking the methylation specific restriction enzyme site—serves mainly to increase the sensitivity of the assay.

Microarray-mediated methylation assay (MMMA) can achieve high sensitivity and high specificity. MMMA performance does not require subjective evaluation of assay data, making its results observer-independent.

MMMA was used for methylation detection. A limited number of GCGC sites in each gene is evaluated by this approach (Melnikov et al., 2005, Nucl. Acids Res. 33:e93), so in some embodiments, choosing a different set of sites within the same set of genes can affect the final readout. Accordingly, in some embodiments, a variety of sets of sites within the same set of genes is utilized. This feature of the assay indicates that, in some embodiments, assignment of "methylated" or "unmethylated" values depends on the selection of the GCGC sites within each region.

Signal detection in MMMA is based in part on competitive hybridization of two PCR products (one from digested and the second from undigested DNA of the same sample), which are labeled with different fluorophores, so that hybridization results are scored as fluorescence intensity for each of them. Assignment of "methylated" (M) and "unmethylated" (UM) calls depends on the ratio of fluorescence of undigested and digested DNA, which produce one of two values; 1, if the fragment is methylated and digestion does not affect its representation, and infinity, if the fragment is unmethylated and no signal from digested DNA is detected. This type of ideal distribution is rarely seen even in cell lines because of intrinsic heterogeneity of biological material.

Additional complications may be associated with the unequal performance of fluorophores Cy3 and Cy5, which ideally should not influence signal distribution, but in reality can affect the results. To adjust results, a "self-self" hybridization is sometimes used for expression microarrays when aliquots of the same DNA sample are labeled separately with Cy3 and Cy5 fluorescent dyes and co-hybridized to the same microarray. Thus, in some embodiments, a similar adjustment is done for methylation detection, so the Cy5/Cy3 ratio from two identical aliquots can be used as the threshold of methylated fragments. Using this approach it is possible to convert numerical data of microarray experiments to binary readout defining methylated and unmethylated calls. It is contemplated that any method that detects the presence or absence of DNA methylation is suitable for uses described herein.

Monitoring treatment effects and rapid screening of a high-risk population is possible by detection of differences in expression profiles when inadequate quantities of starting material are available. The method includes extensive digestion of genomic DNA with a methylation-sensitive restriction enzyme (e.g., HpaII or Hin6I), followed by amplification of gene-specific DNA fragments, which optionally may include multiplex amplification. Optionally, the amplified DNA may include one or more CpG-containing sequences (or CpG islands) which are not digested by the methylation-sensitive restriction enzyme.

When used to characterize, diagnose disease or monitor treatment effects, the degree of DNA methylation may be detected by any appropriate methodology or technology, including any future developed technologies that identify differentially methylated DNA sequences.

Abnormal DNA methylation is observed in certain promoters of neoplastic cells, although the likelihood of methylation for each individual promoter varies. Simultaneous analysis of many promoters in the same sample can allow use of statistical methods for identification of neoplasia. An analysis, based on digestion of genomic DNA with methylation-sensitive restriction enzyme and multiplexed PCR with gene-specific primers (MSRE-PCR). MSRE-PCR includes extensive digestion of genomic DNA (uncut fragments cannot be identified by PCR), applied to dilute samples (<1 pg/µl), requires limited amount of starting material (42 pg or genomic equivalent of seven cells) and can identify methylation in a heterogeneous mix containing <2% of cells with methylated fragments. For example, when applied to 53 promoters of breast cancer cell lines MCF-7, MDA-MB-231 and T47D, MSRE-PCR correctly identified the methylation status of genes analyzed by other techniques. For selected genes, results of MSRE-PCR were confirmed by methylation-specific PCR and bisulfite sequencing. The assay can be configured for any number of desired targets in any user-defined set of genes.

Example 1

Multiple Sclerosis

A method of characterizing a neuroinflammatory demyelinating disease, includes methods for providing a biological sample from a subject diagnosed with the neuroinflammatory demyelinating disease (the biological sample includes genomic DNA) and detecting the presence or absence of DNA methylation in one or more genes or one or more sets of genes, examples of which are listed in Table 1 characterize a neuroinflammatory demyelinating disease in the subject. In some embodiments, the methylation status of the promoter region of the gene is investigated.

There is an unmet need for accessible, inexpensive, and objective biomarkers for multiple sclerosis (MS) as a metric for the disease. Such biomarkers should ideally distinguish MS after the initial clinically isolated syndrome and before additional lesions develop in the CNS. They should also identify imminent exacerbations before clinical symptoms develop and additional CNS damage has already occurred. Ideally, such biomarkers should also identify exacerbations that do not produce clinical symptoms but nonetheless create damage of the CNS as evidenced by asymptomatic gadolinium-enhanced lesions.

Concurrent analysis of DNA methylation in multiple genes using cell-free circulating DNA from plasma of patients with multiple sclerosis identified a set of genes that were differentially methylated in healthy controls and patients treated with anti-MS drug. A set of the most differentially methylated genes provided sensitivity of 96% and specificity of 81% for detection of response to MS treatment.

Clinical specimens. Plasma was collected from patients with recurring-remitting multiple sclerosis (RRMS) treated with Tysabri® and RRMS patients (in remission) that did not receive any treatment.

DNA isolation. DNA from plasma (0.2 ml) was purified using DNAzol reagent (Molecular Research Center, Cincinnati, Ohio, USA).

Microarray mediated methylation assay: Overall approach. The assay for methylation analysis (MethDet test) was initially developed using gel-based detection (methylation-sensitive restriction enzyme digestion with PCR or MSRE-PCR) (Melnikov, 2005). To increase throughput, microarray-based detection was adopted (microarray mediated methylation assay or M3-assay) (Melnikov, 2008). In the MethDet test, one portion of each genomic DNA sample was digested with a methylation-sensitive restriction enzyme while another portion of the same sample served as a control. Selected regions of the genomic DNA from each of the digested and undigested DNA samples were amplified by PCR using gene-specific primers that flank designated restriction sites. In the digested portion, only fragments with methylated sites were resistant to digestion and were capable to serve as templates, whereas in the undigested (control) portion, all fragments were amplified. The two sets of PCR products were compared by competitive hybridization to custom-designed microarrays (M3-assay) (Melnikov, 2008). Fluorescent signals of hybridized fragments in the M3-assay were separately scored, and the ratio between the signals from control and digested DNAs was calculated. This ratio was used to assign methylated or unmethylated "calls". The data were statistically assessed to select groups of informative genes, which were then analyzed together as a composite biomarker. Detailed description of the method is presented in Melnikov et al (Melnikov, 2008).

Statistical analysis. Methylation calls were made independently for each spot, and final gene-specific calls were made according to the majority call from the triplicate spots for that gene. If there was no majority, the final call was NA. As with expression microarray analysis (Scholtens et al. (2005) Analysis of differential gene expression., in Studies in Bioinformatics and Computational Biology Solutions using R and Bioconductor, H.W. Gentleman R, Irizarry R, Dudoit S, Editor.Springer.) non-specific filtering removed uninformative spots (detectable calls in less than ⅔ of the samples or less than 10% differential methylation across the entire sample set). Informative genes with $p<0.10$ were selected by Fisher's Exact Test for differential methylation in gene-specific analyses comparing methylation status for cancer and normal samples. The moderate p-value of 0.10 was chosen to include informative genes with occasionally inflated p-values due to random subsetting of the data in cross-validation. The previously reported independence of methylation sites (Model, et al. (2001), Feature selection for DNA methylation based cancer classification. Bioinformatics, 17 Suppl. 1: p. S157-164.), also evident in these samples, suggested use of the naïve Bayes classifier (Domingos, et al.(1997) On the optimality of the simple Bayesian classifier under zero- one loss. Machine Learning, 29 (2-3): p. 103-130.). Naïve Bayes classifiers were constructed using the e1071 R (R Development Core Team, 2005) package (Gentleman, et al. (2004) Bioconductor: open software development for computational biology and bioinformatics. Genome Biol. (2004), 5:R80.), using an uninformative prior with probabilities of 0.5 for normal or cancer classification. The sensitivity and specificity of the naïve Bayes classifier were estimated using 25 rounds of five-fold cross-validation. For each round of cross-validation, the data were partitioned into five sets with an equal distribution of diseased and control specimens. Each set then served as a test set based on training of the naïve Bayes classifier with the other four sets. Sensitivity and specificity were estimated and averaged over all five runs and over 25 random partitioning of the data into five groups. Gene selection and classifier parameter estimation were performed anew with each round of cross-validation.

Treated samples were correctly identified in 96% of cases. Untreated samples were correctly identified in 81.8% of cases.

| | MS-T vs MS-U | | |
|---|---|---|---|
| | Total number of classified | Correctly classified | Misclassified |
| MS-U | 625 | 511 (81.8%) | 114 |
| MS-T | 625 | 600 (96.0%) | 25 |

Multiple sclerosis methylation profiling is seen in Table 1. Genes studied include CASP8, ERaA, HMLH1, ICAM1, MCJ, MSH2, MYF3, P16, P57, PR-2D, RAR, RASS, RB1 and S100. The graph demonstrates the ratio of unmethylated genes relative to the methylation status of their normal counterpart. The genes demonstrating decreased methylation in multiple sclerosis as compared to patients without multiple sclerosis include CASP8, ERaA, ICAM1, P16, P57, PR-2D, RAR, RASS, RB1 and S100, whereas the converse is true with the genes HMLH1, MCJ, MSH2 and MYF3. Table 1 shows distinctive gene methylation patterns for multiple sclerosis, thereby allowing for profiling, diagnosing, and characterization of this disease.

Table 1 shows the differences in methylated genes between normal blood (controls), blood from subjects with multiple sclerosis (MS-U), and blood from subjects with multiple sclerosis treated with Tysabri (MS-T).

Using MethDet-12k 356 fragments were identified that are unmethylated in healthy age- and gender-matched controls and methylated in patients with multiple sclerosis (Um/M type of fragments) and 47 fragments that are methylated in controls and unmethylated in patients (M/Um type) for a total of 403 differentially methylated fragments. In this set, 61 fragment (15.1%) contain multiple sites of Hin6I and were excluded form further analysis, leaving 342 fragments as potential pool for biomarker selection. Initially seven selected fragments correctly identified 30/30 plasma samples from individuals with the established disease, and 35/35 plasma samples from healthy controls.

Example 2

Breast Cancer Results

Evidence that primary tumor removal and drug treatment induce changes in methylation signature comes from experiments with plasma from invasive breast cancer patients. Plasma was collected from women with breast cancer before and after tumor removal, and then 1-2 years after treatment with Drug 1 (twenty samples per group were analyzed). The data suggests that methylation signatures in plasma do indeed change soon after primary tumor resection and may be useful for detection of residual or recurring tumors. It is also remarkable that treatment with drug 1 induces changes in the methylation signature, so that monitoring of drug efficacy becomes feasible (NB: different genes have been identified in these experiments; percentage of samples with Methylated score for each gene is shown). Changes in methylation induced by therapy also strongly suggest that methylation signatures of responders and non-responders may be different.

Tables 2 and 3 show results for breast cancer comparison.

Example 3

Results for Ovarian Cancer (Using the MethDet-56 Platform)

Ovarian cancer cell-free circulating DNA contains methylation abnormalities observed in primary tumors.

Results for ovarian cancer (using the MethDet-56 Platform indicate that cancer patients (serous papillary adenocarcinoma) have a different methylation profile in their cfpDNA compared to healthy controls. Methylation is different in ~20% of tested genes (11 out of 56) when methylation patterns of cfpDNA are compared for women with malignant and benign masses. Importantly, 7 out of 11 differentially methylated genes are very specific for either benign (genes 1,5-7) or malignant (genes 4, 8, 10) tumors. Based on the number of genes with significant differences in methylation in these preliminary experiments—if the same fraction (20%) of the MethDet-12k genes are differentially methylated, the expectation is to see over 2,400 genes as potential components of the composite biomarker. As noted below, these genes will provide the overall pool for selection of the most differentially methylated genes that will generate the most robust and accurate biomarker with the least components possible.

Methylation is very different in benign and malignant tumors. Methylation analysis of cell-free plasma DNA can produce a simple but robust biomarker for diagnosis. Indeed, biostatistical analysis indicates that diagnosis of ovarian cancer and benign ovarian tumors is possible (Table 6). With analysis of just 56 genes, the upper limits of the 95% credible interval approach or exceed 90% for both sensitivity and specificity. Most of differentially methylated genes identified previously have been confirmed as components of the independent composite biomarker for cancer detection.

First, the MethDet-56 results have identified gene promoters that are differentially methylated between healthy and tumor samples and provided a ranking of differences for selection of the most differentially methylated promoters. Second, the MethDet-56 approach has shown that composite biomarkers have a higher accuracy for disease identification than individual components of these biomarkers.

Methylation anomalies are different for different promoters and suggests that the most divergently methylated promoters will produce exceptionally accurate biomarkers.

The average difference in methylation between healthy subjects and specimens from ovarian cancer patients for the top $1/10$ of tested genes has been 30%. Assuming that $1/10$ of the tested genes will exhibit the same level of differential methylation, 10% of the MethDet-12k components (1,200 genes) will show a 30% differential methylation between cases and controls. If the trend continues, $1/10$ of these (120 genes) can be expected to have a 60% difference, and 12 genes—a 90% difference suggesting that several genes with a very high degree of differential methylation will be useful.

Proteins (e.g. CA125, HE4, cytokines or autoantibodies), microRNA, metabolites, etc—can be easily incorporated in the biomarker. This flexibility is inherent to the MethDet approach and will be very useful to improve and enhance the MethDet-12k biomarkers.

One histological type of ovarian cancer (epithelial cancer—serous papillary adenocarcinoma) has a higher incidence than other major types of epithelial ovarian tumors (endometroid, mucinous, clear cell). Comparisons are made of methylation profiles, e.g., among women with ovarian cancer, benign ovarian disease, and healthy age and ethnicity matched controls.

Materials and Methods

Methylation Profile:

"Methylation profile" (:signature") refers to a presentation of methylation status of one or more marker genes in a subject's genomic DNA. In some embodiments, the methylation profile is compared to a standard methylation profile comprising a methylation profile from a known type of sample (e.g., from a patient with a neuroinflammatory disease either treated or untreated) cancerous or non-cancerous samples or samples from different stages of cancer) treatment or untreated samples from neurological disease. The profile may be presented as a graphical representation (e.g., on paper or on a computer screen), a physical representation (e.g., a gel or array) or a digital representation stored in computer memory. Percent methylation of each gene compared among various clinical groups, is one method to construct a profile.

Clinical Specimens:

Plasma was collected from patients with recurring-remitting multiple sclerosis (RRMS) treated with Tysabri® or Avonex® and RRMS patients (in remission) that did not receive any treatment.

DNA Isolation:

DNA from plasma (0.2 ml) was purified using DNAzol reagent (Molecular Research Center, Cincinnati, Ohio, USA).

Microarray Mediated Methylation Assay: Overall Approach:

The assay for methylation analysis (MethDet test) was initially developed using gel-based detection (methylation-sensitive restriction enzyme digestion with PCR or MSRE-PCR) (Melnikov, 2005). To increase throughput, microarray-based detection was adopted (microarray mediated methylation assay or M3-assay) (Melnikov, 2008). In the MethDet test, one portion of each genomic DNA sample was digested with a methylation-sensitive restriction enzyme while another portion of the same sample served as a control. Selected regions of the genomic DNA from each of the digested and undigested DNA samples were amplified by PCR using gene-specific primers that flank designated restriction sites. In the digested portion, only fragments with methylated sites were resistant to digestion and were capable to serve as templates, whereas in the undigested (control) portion, all fragments were amplified. The two sets of PCR products was compared by competitive hybridization to custom-designed microarrays (M3-assay). Fluorescent signals of hybridized fragments in the M3-assay were separately scored, and the ratio between the signals from control and digested DNAs was calculated. This ratio was used to assign methylated or unmethylated "calls". The data were statistically assessed to select groups of informative genes, which were then analyzed together as a composite biomarker.

Statistical Analysis:

Statistical algorithms for biomarker selection and assessment have been developed for the MethDet-56 platform, have been tested in multiple projects, and are directly applicable to results produced by the MethDet-12k. They include Fisher's exact test to select differentially methylated genes, naïve Bayes algorithm for biomarker selection, and k-fold cross-validation to evaluate performance of the biomarker. Cohen's Kappa coefficient (or Kappa agreement coefficient) will be used to compare results of MethDet-12k with results of a simplified test, performance of the test in the hands of an untrained technician, and results from two different laboratories.

Methylation calls were made independently for each spot, and final gene-specific calls were made according to the majority call from the triplicate spots for that gene. If there was no majority, the final call was non-applicable. A spot is a small area on an array slide that contains a DNA sample with a specific sequence. A majority is a subset of a group that is more than half of the entire group. A call is a determination of the methylation status for a DNA fragment corresponding to a specific spot. A majority call is a call present in more than half of the entire group of calls for a specific DNA fragment. Triplicate spots is a replication of the same spot three times. A replication is the repetition of a condition so that the variability associated with the phenomenon can be estimated.

As with expression microarray analysis (Scholtens, 2005) non-specific filtering removed uninformative spots (detectable calls in less than ⅔ of the samples or less than 10% differential methylation across the entire sample set). Informative genes with $p<0.10$ were selected by Fisher's Exact Test for differential methylation in gene-specific analyses comparing methylation status for diseases and normal (non-diseased) samples. The moderate p-value of 0.10 was chosen to include informative genes with occasionally inflated p-values due to random subsetting of the data in cross-validation. The previously reported independence of methylation sites (Model, 2001), also evident in present samples, suggested use of the naïve Bayes classifier (Domingos, 1997). Naïve Bayes classifiers were constructed using the e1071 R (R Development Core Team, 2005) package (Gentleman, 2004), using an uninformative prior with probabilities of 0.5 for normal or disease classification. The sensitivity and specificity of the naïve Bayes classifier were estimated using 25 rounds of five-fold cross-validation. For each round of cross-validation, the data were partitioned into five sets with an equal distribution of diseased and control specimens. Each set then served as a test set based on training of the naïve Bayes classifier with the other four sets. Sensitivity and specificity were estimated and averaged over all five runs and over 25 random partitioning of the data into five groups. Gene selection and classifier parameter estimation were performed anew with each round of cross-validation.

Statistical Algorithm to Classify Blinded Samples.

Naïve Bayes Classification approach is used to classify blinded samples and validate accuracy of the diagnosis. Differentially methylated genes that constitute the biomarker are identified, and frequency of methylation established for each of them. These frequencies are used as classification parameters (conditional probabilities, $P_c$) for the validation. Each gene (i) of the k genes selected for the biomarker have two conditional probabilities of methylation established, one—for cancer samples, $P_c(g_i/C)$, and another—for samples from patients without cancer, $P_c(g_i/nC)$. For each sample in the validation set, two posterior probabilities are calculated according to the methylation status of the selected genes: $P(C/g_1, \ldots g_k)$ for cancer; $P(nC/g_1, \ldots, g_k)$ for non-cancer. These two probabilities will be compared to determine which group the sample belongs to: if $P(C/g_1, \ldots, g_k) > P(nC/g_1, \ldots, g_k)$, the sample is classified as cancer, otherwise—as non-cancer. Each of the two posterior probabilities equals to a product of the k conditional probabilities, a prior probability, $P(C)$ or $P(nC)$, and a joint probability, $P(g_1, \ldots,$ $g_k$). If in the validation set cancer and non-cancer samples are equally presented, then P(C)=P(nC), and two products will be compared:

$$P(C/g1,\ldots gk)=P(C)*[Pc(g1/C)*Pc(g2/C)*\ldots*Pc(gk/C)]/P(g1,\ldots,gk);$$

and $$P(nC/g1,\ldots,gk)=P(nC)*[Pc(g1/nC)*Pc(g2/nC)*\ldots*Pc(gk/nC)]/P(g1,\ldots,gk);$$

Since joint probability, $P(g_1, \ldots, g_k)$, is a constant for both groups, and cancer and non-cancer samples are equally presented, ie., P(C)=P(nC), only two products need to be compared:

$$[P_c(g_1/C)*P_c(g_2/C)*\ldots*P_c(g_k/c)] \text{ vs } [P_c(g_1/nC)*P_c(g_2/nC)*\ldots*P_c(g_k/nC)].$$

In these equations, if a gene (i) is not methylated, the corresponding conditional probability $P_c(g_i/.)$ is replaced by $1-P_c(g_i/.)$. When this classifier is applied to testing of patients, prior probabilities P(C) and P(nC) will be included into the equations.

Results of the blinded set test are used to improve the classification scheme. Since each patient has two posterior probabilities, a difference between them is calculated. Then the distribution of all the differences, as well as distribution of differences from correctly classified and mis-classified samples from the blinded set are explored to define an area of potential uncertainty. Receiver operating characteristic (ROC)—area under the curve (AUC) approach is used to select the best cut-off value.

Biological Samples

A suitable biological sample is a plasma sample, a biological fluid (e.g., CSF). The DNA methylation includes a method of CpG methylation detecting the presence or absence of DNA methylation, for example, includes the digestion of genomic DNA with a methylation-sensitive restriction enzyme followed by amplification of gene-specific DNA fragments, which optionally may include multiplex amplification. Optionally, the amplified DNA may include one or more CpG-containing sequences (or CpG islands) which are not digested by the methylation-sensitive restriction enzyme. Suitable methylation-sensitive restriction enzymes include AciI, HpyCH4IV, Hin6I and HpaII. Neuroinflammatory demyelinating diseases include multiple sclerosis, transverse myelitis, optic neuritis, acute dessiminated encephalomyelitis Guillain-Barre syndrome, chromic inflammatory demyelinating polyneuritis, or progressive multifocal leukoencephalopathy. Any method for detection of DNA methylation is contemplated for use in the methods of the present invention including those found in Liu and Maekawa, 2003 Anal. Biochem, 314:259-65, and U.S. Pat. Nos. 7,144,701, 7,112,404, 7,037,650, 6,214,556 and 5,786,146, all herein incorporated by reference in their entireties.

Kits

A kit for characterizing a neuroinflammatory demyelinating disease, includes reagents for (e.g., sufficient for) detecting the presence or absence of DNA methylation in one or more genes listed in Table 1 Instructions for using the kit for characterizing a neuroinflammatory demyelinating disease in the subject are included and the instructions required by the United States Food and Drug Administration for use in in vitro diagnostic products. The reagents include reagents for digestion of the genomic DNA with a methylation-sensitive restriction enzyme followed by amplification of gene-specific DNA fragments, which optionally may include multiplex amplification. Optionally, the amplified DNA may include one or more CpG-containing sequences (or CpG islands) which are not digested by the methylation-sensitive restriction enzyme. In embodiments, characterizing a neuroinflammatory demyelinating disease includes determining the risk of developing a neuroinflammatory demyelinating disease. In yet other embodiments, characterizing a neuroinflammatory demyelinating disease includes monitoring disease progression in the subject and monitoring treatment effects.

The biological sample tested from a subject is tested for the presence or absence of DNA methylation in one or more (e.g., 2, 3, 4, 5, 6, 7, 8, 9, 10, 11, 12, 13, 14) of the following genes; CASP8, ERaA, HMLH1, ICAM1, MCJ, MSH2, MYF3, P16, P57, PR-2D, RAR, RASS, RB1 and 5100. See Table 1.

The methods described herein are useful in conjunction with other methods for monitoring a neuroinflammatory demyelinating disease. For example, a MS methylation profile as described herein can be used by a diagnostician in conjunction with results from a MRI of the brain or spine, results of tests run on cerebral spinal fluid, results from VEP and/or SEP analysis, presence of anti-myelin proteins, and other tests used to monitor MS in a patient. A MS methylation profile is used to diagnose disease in a patient at an early stage wherein the aforementioned diagnostic tests would normally yield negative diagnostic test results for MS. With an earlier diagnosis than previously possible, treatment regimens can be given to a subject much sooner, thereby potentially inhibiting progression of the disease at an earlier stage than was otherwise possible with current diagnostic methods and procedures.

General Experimental Outline

Purified genomic DNA from plasma samples is divided into two parts; one of the samples is treated with the methylation-sensitive restriction enzyme Hin6I while the other one is used as a control. Both control and digested DNA are used as templates for nested PCR with aminoallyl-dUTP added at the second round of amplification. Following amplification, the incorporated aminoallyl-dUTP is coupled to reactive Cy5 or Cy3 dyes, creating fluorescently labeled probes. One of the dyes is used for PCR products from undigested control DNA, while another is used for PCR products from Hin6I-digested DNA. Both labeled products are mixed together and applied to a custom-designed microarray slide for competitive hybridization. A microarray reader is used to quantify fluorescence of each fluorophore in every spot of the array, and the Cy5/Cy3 ratio used to assess methylation status. Methylated fragments produce Cy5/Cy3 ratios close to 1, while unmethylated fragments have ratios higher than 1. Statistical analysis of hybridization data is performed to identify informative features and build the classifier for each disease marker panel.

Restriction Enzyme Digestion of Tissues

Exhaustive digestion of DNA is done with the methylation sensitive restriction endonuclease Hin6I (Fermentas International, Inc., recognition site GCGC). Successful digestion of 4 ng of DNA is done with 40 U of the enzyme in 100.mu.l of reaction mix at 37° C. for 48 hours. To exclude non-specific degradation of DNA during a long incubation we use the second aliquot of DNA incubated without the enzyme. This control is then processed side-by-side with digested DNA and only fragments with an adequate signal from control DNA are scored. After digestion is completed, the DNA is purified and quantitated.

PCR Amplification of Sample DNA

The first round of PCR amplification, nested PCR, is performed using 400 pg of digested and control DNAs. Empirically assembled primer groups for multiplex reactions allow simultaneous amplification of five targets in each reaction.

Final concentration of primers is 0.2.mu.M for each of the multiplex PCR reactions. KlenTaq® 1 (DNA Polymerase Technology, Inc) is used at 20 U per 50.mu.l reaction. To PCR buffer supplied with the enzyme we add betaine (Sigma) to 1.5M and dNTPs (Sigma) to 0.25 mM. The tubes are placed into a preheated ABI 9600 thermocycler and incubated for 5 min prior to addition of KlenTaq® 1. PCR is started for 25 cycles by initial denaturation at 95° C. followed by 25 cycles of; 45 sec—62° C.; 1 min—72° C.; 1 min cycling conditions. After 25 cycles the PCR reactions are kept at 4° C.

The PCR products of the first round are purified using QIAquick® PCR Purification Kit (Qiagen) and quantified. Amplification products for corresponding DNAs are combined, and 400 pg are used for the second PCR, which is assembled as above except for dNTPs, where a mix of aminoallyl-dUTP (Biotium, Inc,) and dTTP (3:1) is used. The second round of PCR is performed as the first except only 20 cycles are used. PCR products are purified using QIAquick® PCR Purification Kit and products are combined.

The second PCR products are dried in vacuum and dissolved in 5.mu.l of 200 mM NaHCO.sub.3 buffer (pH 9.0). Cy3 or Cy5 fluorescent dyes in DMSO are added to each tube, mixed and spun. Labeling continues for two hours at room temperature in the dark. Unreacted Cy dyes are quenched by 4.5.mu.l 4M hydroxylamine for 15 minutes in the dark. Final purification is done by precipitating labeled PCR products with ethanol.

Development and Manufacture of the Array

Oligonucleotide arrays are custom designed by Microarrays, Inc (Nashville, Tenn.). Probes for the array are 50-60 mers to keep hybridization and washing temperatures high (Relogio et al., 2002, Nucleic Acids Res 30:e51). Probes have been designed according to the Affymetrix model (Mei et al., 2003, PNAS 10:11237-11242). Controls may be present on the array, for example: (1) transcribed regions from *Arabidopsis thaliana* (definitive negative control, heterologous); (2) transcribed regions of human α-tubulin, β-actin and glyceraidehyde-phosphate-dehydrogenase (GAPDH, definitive negative controls, homologous); (3) promoters of β-actin, phosphoglycerate kinase (PGK1) and/or ribosomal protein L15 (conditional homologous negative control). HPLC-purified oligonucleotides with an amino group and a six-carbon spacer at the 5'-end are spotted on aminosilane-modified glass slides in triplicate, so each slide contains three identical subarrays. Attachment of the probe is done by incubation at 60° C. for 3.5 hr and for 10 min at 120° C. Slides are stored under vacuum in the dark at room temperature. Genes to be tested in the DNA methylation assay include those listed in Table 1 that are specific to the method being performed. These genes represent different functional groups; all of them have been identified as methylated in different disease states.

Probe Hybridizations with Microarray

Competitive hybridization of the PCR probes to oligonucleotide arrays is done in rotating tubes in the hybridization chamber. The slides are pre-hybridized for 1 hr at 42° C. in 5×SSC, 0.1% SDS, 1% BSA, rinsed with deionized water and dried by short centrifugation. Hybridization space is created on the slide by Microarray GeneFrames (AbGene, Rochester, N.Y.). Denatured DNA is added to the array, the coverslip is sealed, and the slides are incubated in the dark at 42° C. for 18 hr. After hybridization the GeneFrame and the coverslip are removed, and the slides are washed with shaking in a set of buffers heated to 42° C. 5 min in 1.times.SSC, 0.1% SDS; 5 min in 0.1.times.SSC, 0.1% SDS; 3 min in 0.1.times.SSC, 0.1% SDS. Slides are dried by a short, low-speed centrifugation and stored in the dark before scanning.

During optimization of the procedure, a single PCR product was labeled with two different fluorophores, probes were mixed, and used for hybridization. In this mixture Cy5- and Cy3-labeled fragments were represented equally imitating conditions for methylated fragments. Mean Cy5/Cy3 ratio calculated from such experiments produced the normalization coefficient to account for fluorophore-related differences in labeling and detection.

Signal Detection and Sample Scoring

Scanning is done with ScanArray™ 4000XL (Packard BioChip) or GenePix4000B (Molecular Devices) or another scanner for microarrays according to the manual. The protocol for detection of two fluorophore hybridizations is used.

Initially the signals are normalized to account for differences in fluorophore incorporation and detection. The percentage of the signal for an individual spot relative to the total signal from the corresponding fluorophore is used to normalize signals across the array and then the ratio of the Cy5/Cy3 percentages for each spot is computed. An alternative technique makes use of the expected distribution of the ratios and allows for differences in methylation status at the majority of sites under investigation. Suppose we observe $(x_1, y_1)$, $i=1, \ldots, n$ where $x_1$ is the Cy3 intensity and $y_1$ is the Cy5 intensity for specimen i. The goal of normalization is to find a function, f(.) such that $y_1 \mathrm{gtoreq.} f(x_1)$, for most of the regions. A smoothed lower boundary for the cloud $(x_1, y_1)$, $i=1, \ldots, n$ can be achieved by non-parametric quantile regression in which the 10-20% quantile curve is used as the normalizing function f(.). Such a function will allow measurement error so that some $y_1$ values may be slightly less than $f(x_1)$. In the end, the ratio $r_1 = y_1/f(x_1)$ is then used to measure the signal. This technique will produce ratios that are either close to 1 or >1 and will reduce the number of methylation sites with middle range ratios (1.3 to 2). After the signals are normalized, ratios will be computed.

The percentage normalization method allows the detection of very high Cy3:Cy5 ratios (up to 5,000) and approximately equal ratios (between 0.8 and 1.2), which correspond to unmethylated and methylated sites, respectively. Some genes fall in the intermediate range (genes methylated in some part of the population with ratios between 1.3 and 2) and are removed from the diagnostic set. The quantile regression normalization method eliminates these intermediate values, so no manual adjustment is required.

The pattern of expression microarray analysis is followed and non-specific filtering is applied to remove uninvolved or uninformative features from consideration before selecting the most divergent in their methylation status (Scholtens and von Heydebreck (2005). Two non-specific filters are applied: 1) for all samples investigated, 80% of the samples must give interpretable ratios (<1.3 or >2); and 2) at least 10% differential methylation must be observed across all samples (e.g., 90% methylated and 10% unmethylated). After the non-specific filtering step, methylation sites (features) are selected on the basis of differential status in the test and control tissues. The naïve Bayes algorithm for pattern recognition (Domingos and Pazzani (1997) will be used to identify genes for the composite biomarker and then ten-fold cross-validation (Vehtari and Lampinen (2002) Bayesian model assessment and comparison using cross-validation predictive densities. Neural Comput, 14:2439-2468.) will be used to assess its performance. In a ten-fold cross-validation, the data are randomly partitioned into ten subgroups, of which one subgroup is retained for validation, and the remaining nine subgroups are used for training. The naïve Bayes algorithm is applied to the training set to select genes for the composite biomarker, which is then used with the validation set. The cross-validation process is repeated ten times (the folds), with each of the ten subgroups used exactly once as the validation data. This whole cycle is then repeated 25 times, producing 250 (25×10) composite biomarkers with associated performance data (sensitivity, specificity, misclassification rate, and relative classifier information). The final biomarker will include genes selected in over 75% of 25 rounds.

DNA-Based Biomarkers.

Accuracy of the test relies on the sensitivity of the assay and that in turn depends on the nature of the analyte. In this respect protein-based assays can be not as sensitive as DNA-based tests—DNA amplification by polymerase chain reaction (PCR) detects a single copy of DNA, which may be difficult to match for protein-based assays.

DNA-based testing does not have to evaluate genetic changes; it can be based on epigenetic modifications of DNA. Methylation of cytosines in cytidine-guanosine dinucleotides (CpG) is the most frequent epigenetic event, and multiple genes are known to be abnormally methylated in ovarian cancer. A test based on this abnormal methylation would have solved the problem of cancer detection if any gene(s) was known to be always methylated in one condition, and unmethylated in others. Unfortunately, such a gene has yet to be found, and the general redundancy of regulatory pathways argues against this possibility. Indeed, there is no single gene consistently methylated even when tumors are compared to healthy tissues, so a single gene-based assay is unlikely the answer. This problem can be resolved if many genes are tested in the same clinical sample, so that the probabilities of methylation are combined to increase accuracy of the test. In this regard, the methylation test follows the logic of composite biomarkers, established for protein assays with the added benefit of simplicity provided by PCR-based analysis of DNA methylation without the need for complex techniques such as mass-spectroscopy.

Links Between the Biomarker Accuracy and the Number of Genes in the Signature.

An ideal biomarker is a single gene that identifies tumors with 100% accuracy. Unfortunately, such a biomarker has not yet been found; instead, the most differentially methylated genes are combined into composite biomarkers, so that several genes contribute to the final result. This combinatorial approach is fraught with the danger of higher background noise and decreased accuracy as the number of genes in the biomarker increases. A special biostatistical approach has been established to solve this problem, which includes several steps: identification of differentially methylated genes in both sample sets (reference and test), ranking the differences, and using a machine learning technique (naïve Bayes algorithm) to select the most informative combination. With this design, the overall number of tested genes does not increase the background noise, because only the most differentially methylated genes are included in the pool for the naïve Bayes algorithm. Only the most differentially methylated genes are considered for the biomarker, so increasing the number of tested genes on the array just increases the initial pool of genes that are considered. After the methylation signature is available, the filtering step for methylation differences removes genes with differential methylation below a certain threshold. This threshold can be adjusted to select the best of the best, so the vast majority of the genes will be removed from consideration and will not increase the background. Instead, increase in the pool of tested genes increases the chances of finding the most informative genes, so genes with the highest level of differential methylation remain. This approach has been designed and confirmed when transitioning from a small number of tested genes to the MethDet-56. The accuracy of breast cancer detection was negligible when a handful of genes were tested in each sample, but improved dramatically with the introduction of the MethDet-56. Another leap in improvement was confirmed with the Meth-Det-12k, with the biomarker for multiple sclerosis.

Benefits and Limitations of the MethDet Platform.

Figure 2:
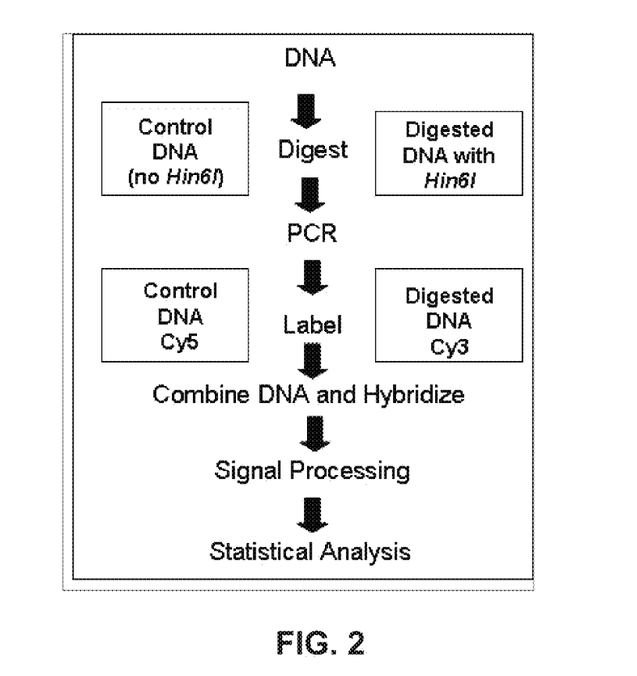
FIG. 2 is a flow chart of the MethDet-56 assay.
Figure 3:
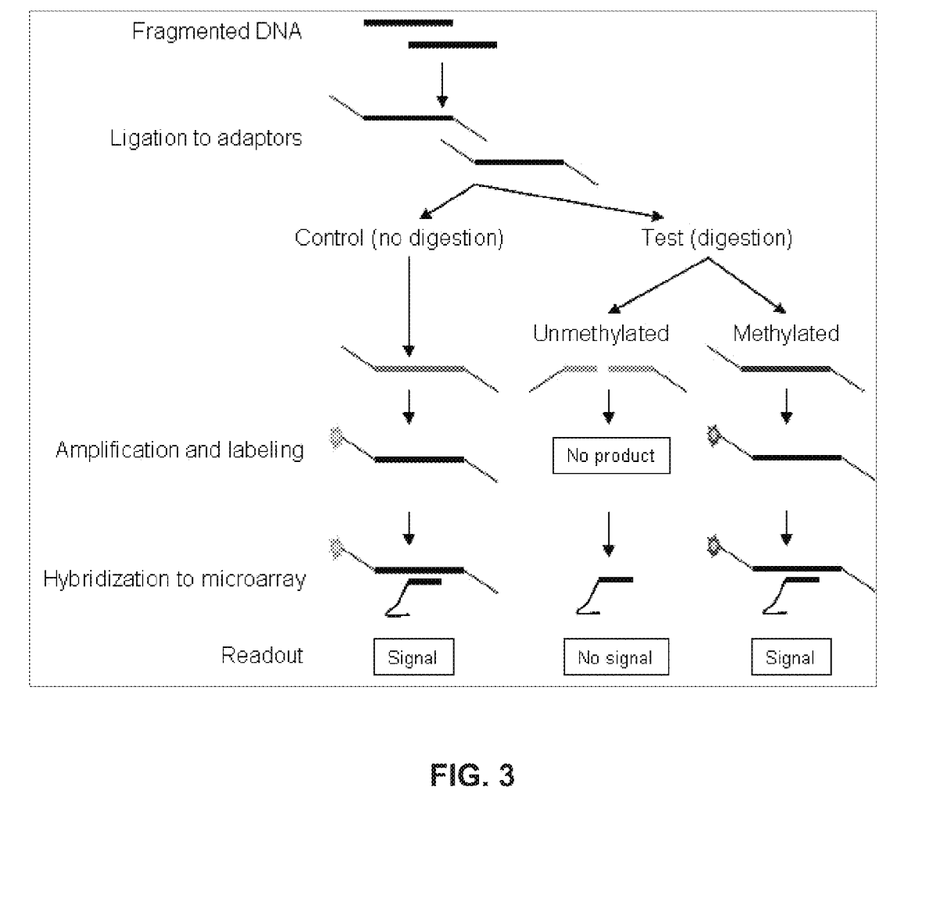
FIG. 3 is a schema of genome-wide methylation assessment.
Figure 4:
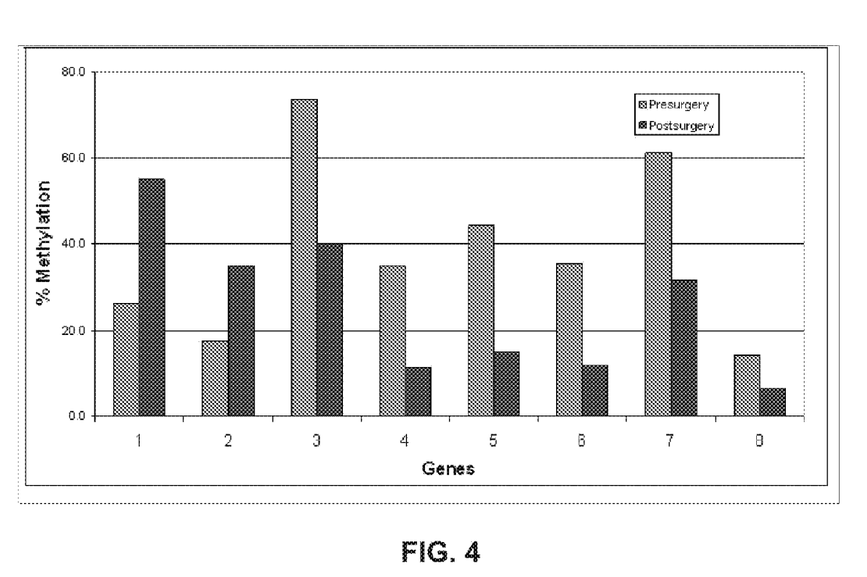
FIG. 4 is a methylation signature in plasma changes after the primary tumor is surgically removed. Analyzed with MethDet-56.
Figure 5:
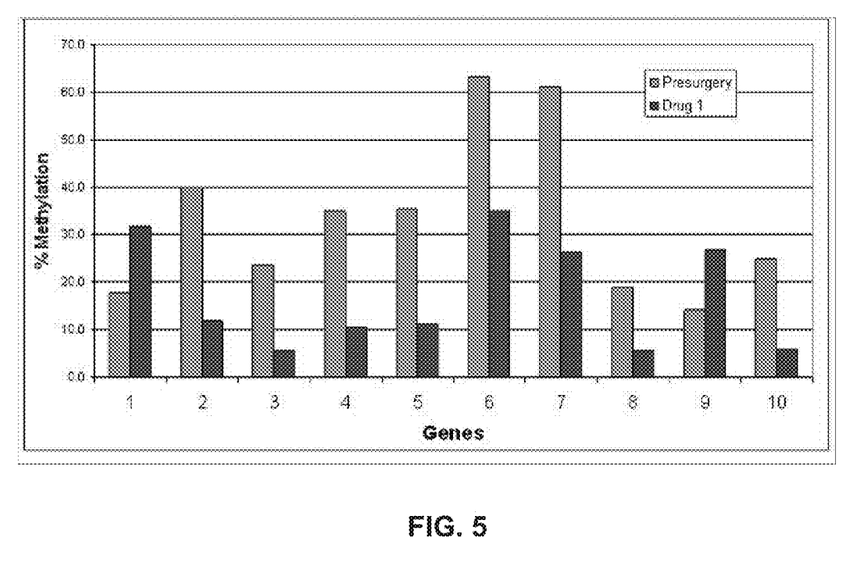
FIG. 5 is methylation signature in plasma changes after treatment with Drug 1. Analyzed with the MethDet-56.
Figure 6:
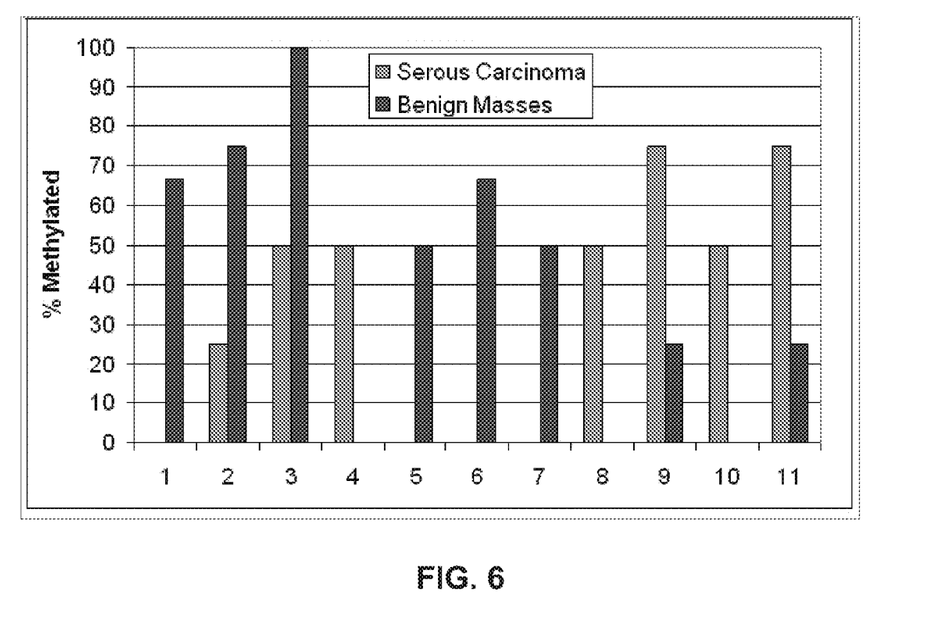
FIG. 6 is differences in methylation signatures identified in plasma for adenocarcinoma of the ovary and benign ovarian masses.

The first generation assay (MethDet-56) demonstrates the approach; its schema is shown in FIG. 2. Purified DNA from a clinical sample is divided into two parts, and one of them is digested by a methylation-sensitive restriction enzyme (Hin6I), while the other is left undigested and serves as a control. Both digested (test) and undigested (control) DNA serve as templates for PCR with gene-specific primers selected to flank chosen Hin6I sites (for the MethDet-12k this step is modified to permit amplification of all fragments. PCR reactions include aminoallyl-dUTP, so once the amplification reaction is finished, PCR products can be labeled with fluorescent dyes—Cy5 for control and Cy3 for test. Next, labeled PCR products are mixed and applied to a custom-designed microarray with probes for amplified fragments (the Meth-Det-12k uses a human CpG-island array. After hybridization Cy5 and Cy3 signals are recorded, and the Cy5/Cy3 ratio is calculated. This ratio fluctuates depending on the ratio of methylated and unmethylated fragments of each kind, so an experimental cutoff value for each fragment has been established. This cutoff is used to separate fragments into methylated and unmethylated groups, which greatly simplifies downstream statistical analysis and allows a streamlined analysis of heterogeneous samples. The cutoff value identifies a fragment as Methylated until the input of unmethylated components is below 50%. After this ratio is above 50%, the fragment is designated as Unmethylated. By ignoring minor variations in the Cy5/Cy3 ratio and binning the data into two bins (Methylated and Unmethylated) a streamlined analysis of heterogeneous samples becomes possible. This binning is another important feature of the MethDet assay, which, to the inventors knowledge, has not yet been tried for methylation marker development.

Methylation can also be detected using bisulfite modification procedure which converts unmethylated cytosines to uracils while leaving methylated cytosines intact. Ensuing changes in DNA sequence are then detected by a variety of methods. The bisulfite technique has its limitations, including a significant—up to 95%—loss of DNA during bisulfite treatment. If milder conditions are used there is a significant danger of incomplete conversion leaving questions about methylation status of some cytosines. On the other hand, all CpG sites can be analyzed, so for abundant and homogeneous samples bisulfite modification can provide a comprehensive picture of methylation. In clinical samples, however, amount of DNA is usually very small, the DNA itself is heterogeneous, and this heterogeneity is likely to be variable. In this situation bisulfite-based techniques become progressively more difficult to perform and less informative. As the result, practical use of bisulfite-based quantitative biomarkers becomes much more challenging than a simple PCR assay of the MethDet technique.

Methylation-sensitive restriction enzyme Hin6I used for the MethDet, does not cut DNA if the first cytosine in the recognition sequence (GCGC) is methylated. As the result, one CpGs site is evaluated for each GCGC. This limitation is compensated for by the abundance of GCGC sites in the genome, so that many genes can be analyzed. To take full advantage of this feature a robust technique for analysis of multiple fragments in each sample is required, so the Meth-Det approach has been developed. The first generation of MethDet assay has worked well and produced valid, stable, and clinically relevant results in the proof-of-principle studies. Results of these studies also indicate that the MethDet-56 platform is underpowered to produce accurate biomarkers for clinical use. This problem is addressed with the MethDet-12k assay, which is expected to produce clinically relevant biomarkers.

The speed and simplicity of the MethDet procedure and its ability to comprehensively test small amounts of DNA are used to select informative biomarker components within heterogeneous clinical samples. In addition, the MethDet procedure is designed as a "top-down" approach and is not limited by restrictions inherent to a "candidate gene" analysis.

Isolation of Plasma.

Blood is collected into purple-top (EDTA) Vacutainer. Immediately after collection the tube is placed on ice, and plasma is isolated within 6 hr by two rounds of centrifugation at 2,500 g for 10 min in a refrigerated laboratory centrifuge. Both times the clear supernatant is collected by a sterile pipette and transferred into a clean tube. After the second centrifugation plasma is separated into a set of tubes pre-labeled with a unique identifier and flash-frozen in liquid nitrogen. Prepared plasma can be stored at −80° C. for at least three years without visible degradation of DNA or changes in its methylation profile (unpublished).

Purification of DNA.

Genomic DNA is isolated from plasma. Briefly, plasma is mixed with an equal volume of $2^x$ Proteinase K digestion buffer (100 mM NaCl, 10 mM TrisHCl, pH8.0, 10 mM EDTA, 0.5% SDS) and incubated at 55° C. for 6 hr with Proteinase K (1 mg/ml final; Sigma-Aldrich, St. Louis, Mo.). DNA is purified using DNAzol reagent (MRC, Cincinnati, Ohio): DNA is mixed with 10 vol of DNAzol, linear polyacrylamide (GenElute, Sigma-Aldrich) is added to 10 μg/ml, and DNA is precipitated by 0.5 vol of 100% ethanol, washed twice with a mixture of DNAzol and ethanol (70:30) and with 80% ethanol. Finally, DNA is dissolved in 10 mM Tris pH7.8, 0.5 mM EDTA. Concentration of DNA is determined using either Hoechst 33248 and DyNAQuant 2000 (Amersham, GE Healthcare, Piscataway, N.J.) or PicoGreen® assay (Invitrogen, Carlsbad, Calif.).

Adapter ligation follows the procedure outlined by Huang and colleagues with several modifications. Briefly, DNA is fragmented by sonication (Branson S-450 sonic disruptor) to achieve average fragment length of 300-500 bp, which will reduce the number of Hin6I sites per fragment and improve PCR amplification. The ends are repaired with T4 DNA polymerase in the presence of excess dNTP. Then Taq polymerase is used to add A to the 3' ends in order to prevent cross-ligation between fragments. Universal adaptors are prepared by annealing two synthetic oligos synthesized to generate one blunt end and one end with T overhang to facilitate ligation to genomic fragments. Both ends are dephosphorylated to prevent self ligation. A ten-fold molar excess of adaptors is used for overnight ligation; in these conditions we have not observed adaptor dimers after PCR, while all fragments have produced signal on the MethDet-12k array.

Hin6I Digestion.

Digestion of DNA with Hin6I (recognition site GCGC; Fermentas, Glen Burnie, Md.) is done as before. Briefly, one ng of DNA is incubated with 40 U of the enzyme in 100 μl of reaction mix at 37° C. for 20 hr; to monitor potential non-specific degradation of DNA the second aliquot of DNA is incubated without the enzyme. This control is then processed side-by-side with digested DNA and only fragments with a signal from control DNA are scored on the microarray.

PCR Amplification:

400 pg of digested and control DNAs are used for PCR with universal primers. Final concentration of primers is 0.5 μM for each of the multiplex PCR reactions. KlenTaq1 (DNA Polymerase Technology, St. Louis, Mo.) is used at 20 U per 50 μl reaction. Standard PCR buffer is supplemented with dNTPs at 0.25 mM and betaine at 1.5M (both—from Sigma). PCR is done for 35 cycles using 95° C.; 45 sec—62° C.; 1 min—72° C.; 1 min cycling conditions, then a mix of aminoallyl-dUTP (Biotium, Inc, Hayward, Calif.) and dTTP (3:1) is added for additional 5 cycles of PCR. PCR products are purified with QIAquick PCR Purification Kit and eluted in water.

Coupling aminiallyl-labeled PCR products to Cy dyes (GE Healthcare) is done. Purified PCR products are dried in vacuum and dissolved in 5 μl of 200 mM NaHCO$_3$ (pH 9.0). Cy3 or Cy5 in DMSO are added to each tube and mixed. Labeling continues for two hours at room temperature in the dark; unreacted Cy dyes are quenched by 4.5 μl 4M hydroxylamine for 15 minutes in the dark. Final purification is done by precipitating labeled PCR products with ethanol.

CpG Array.

The single-spotted arrays are produced by the Microarray Centre (University Health Network, Toronto, ON, Canada). Each array contains 12,192 CpG-island clones produced by the Wellcome Trust Sanger Institute (Edinburgh, UK) as MseI fragments using a methylated DNA binding column. All clones of the library were sequenced at the Wellcome Trust Sanger Institute and subsequently at the Michael Smith Genome Sciences Centre (Vancouver, BC, Canada) and at the Microarray Centre. Arrays contain Arabidopsis controls from the University Health Network Microarray Centre and Stratagene's Spot Report™ Alien™ cDNA Array Validation System (Strategies, 2004, 18 (3), p. 72-73). This System is a set of 10 artificial sequences designed to have no sequence homology with any genome and provide negative controls.

Hybridization with the Array. Competitive hybridization of the PCR products to CpG microarrays is done. The slides are pre-hybridized for 1 hr at 42° C. in 5×SSC, 0.1% SDS, 1% BSA, rinsed with deionized water and dried by short centrifugation. Hybridization space is created on the slide by Microarray GeneFrames (AbGene, Rochester, N.Y.). Denatured DNA is added to the array, the coverslip is sealed, and the slides are incubated in the dark at 42° C. for 18 hr. After hybridization the GeneFrame and the coverslip are removed, and the slides are washed with shaking in a set of buffers heated to 42° C. Slides are dried by a short, low-speed centrifugation and stored in the dark before scanning.

Detection of the Signal.

Scanning is done with GenePix4000B according to the manual (Axon-Molecular Devices, Sunnyvale, Calif.). GenePix Pro 6.0 software allows selection of different photo multiplier tube (PMT) gain parameters to adjust to different quantum yields of Cy3 and Cy5 flourophores; these parameters have been established experimentally based on the maximum signal strength and minimum background/PMT noise. Signal is acquired using simultaneous detection of both fluorophores with 5 μm resolution and linearity of signal over four orders of magnitude. The quality filter requires each spot to have a median-based signal-to-noise ratio of at least 3 for each channel and at least 50 foreground pixels. Spots that do not fulfill these requirements are treated as missing values in the subsequent analysis.

OTHER DEFINITIONS

As used herein, the term "detecting the presence or absence of DNA methylation" refers to the detection of DNA methylation in the promoter or other region of one or more genes (e.g., disease markers of the present invention) of a genomic DNA sample. The detecting may be carried out using any suitable method, including, but not limited to, those disclosed herein.

As used herein, the term "monitoring disease progression in said subject" refers to the monitoring of any aspect of disease progression. In some embodiments, monitoring disease progression comprises determining the DNA methylation pattern of the subject's genomic DNA.

As used herein, the term "methylation profile" refers to a presentation of methylation status of one or more disease marker genes in a subject's genomic DNA. In some embodiments, the methylation profile is compared to a standard methylation profile comprising a methylation profile from a known type of sample (e.g., samples known not to originate from a subject having a disease or samples known to originate from a subject having a specific disease). In some embodiments, methylation profiles are generated using the methods of the present invention. The profile may be presented as a graphical representation (e.g., on paper or on a computer screen), a physical representation (e.g., a gel or array) or a digital representation stored in computer memory.

TABLE 2

BREAST CANCER
Accuracy of breast cancer detection using DNA methylation analysis in plasma

| pCatsTest | Cancer | Normal |
|---|---|---|
| pCancer | 84% (sensitivity) | 20% |
| pNormal | 16% | 80% (specificity) |

TABLE 3

FREQUENCY OF METHYLATION FOR GENES OF THE COMPOSITE BIOMARKER FOR BREAST CANCER

|  | Cancer | Normal |
|---|---|---|
| DAPK | 11% | 49% |
| FAS | 17% | 76% |
| MCT1 | 33% | 71% |
| CDKN2B | 26% | 65% |
| PAX5 | 25% | 60% |
| PGK | 21% | 62.5% |

TABLE 1

| Gene | Methylation in controls, N (%) (n = 26) | Methylation in MS-T, N (%) (n = 25) | P-value: MS_T vs control** | Methylation in MS-U, N (%) (n = 25) | P-value: MS_U vs control** | P-value: MS_T vs MS_U** |
|---|---|---|---|---|---|---|
| BRCA1 | 9 (37.50) | 25 (100.00) | <.0001 | 9 (37.50) | 1.0000 | <.0001 |
| CALCA | 7 (26.92) | 23 (95.83) | <.0001 | 7 (29.17) | 1.0000 | <.0001 |
| CASP8 | 15 (60.00) | 24 (96.00) | 0.0046 | 21 (84.00) | 0.1137 | 0.3487 |
| CCND2 | 7 (29.17) | 21 (87.50) | 0.0001 | 6 (24.00) | 0.7536 | <.0001 |
| DAPK | 7 (26.92) | 24 (96.00) | <.0001 | 9 (36.00) | 0.5551 | <.0001 |
| CDH1 | 5 (19.23) | 24 (100.00) | <.0001 | 15 (62.50) | 0.0034 | 0.0016 |
| EDNRB | 6 (25.00) | 25 (100.00) | <.0001 | 5 (20.83) | 1.0000 | <.0001 |
| EP300 | 8 (32.00) | 25 (100.00) | <.0001 | 8 (33.33) | 1.0000 | <.0001 |
| ESR1 prA | 18 (75.00) | 25 (100.00) | 0.0096 | 19 (79.17) | 1.0000 | 0.0223 |
| ESR1 prB | 16 (61.54) | 25 (100.00) | 0.0007 | 21 (91.30) | 0.0210 | 0.2243 |
| FAS | 15 (57.69) | 24 (96.00) | 0.0020 | 18 (78.26) | 0.1431 | 0.0912 |
| FHIT | 8 (30.77) | 25 (100.00) | <.0001 | 11 (44.00) | 0.3929 | <.0001 |
| NR3C1 | 17 (73.91) | 25 (100.00) | 0.0082 | 20 (83.33) | 0.4936 | 0.0502 |
| HIC1 | 14 (56.00) | 23 (92.00) | 0.0083 | 9 (36.00) | 0.2563 | 0.0001 |
| HIN1 | 24 (92.31) | 25 (100.00) | 0.4902 | 24 (96.00) | 1.0000 | 1.0000 |
| MLH1 | 12 (48.00) | 25 (100.00) | <.0001 | 12 (48.00) | 1.0000 | <.0001 |
| ICAM1 | 12 (48.00) | 23 (92.00) | 0.0015 | 12 (48.00) | 1.0000 | 0.0015 |
| MDGI | 6 (23.08) | 23 (95.83) | <.0001 | 10 (40.00) | 0.2367 | <.0001 |
| MDR1 | 3 (12.00) | 19 (82.61) | <.0001 | 9 (36.00) | 0.0955 | 0.0014 |
| MGMT | 13 (50.00) | 21 (87.50) | 0.0063 | 3 (12.00) | 0.0059 | <.0001 |
| MCJ | 11 (42.31) | 20 (83.33) | 0.0038 | 12 (50.00) | 0.7769 | 0.0305 |
| MSH2 | 10 (38.46) | 25 (100.00) | <.0001 | 7 (29.17) | 0.5592 | <.0001 |
| MUC2 | 19 (73.08) | 25 (100.00) | 0.0098 | 22 (88.00) | 0.2913 | 0.2347 |
| MYF3 | 14 (56.00) | 25 (100.00) | 0.0002 | 11 (44.00) | 0.5721 | <.0001 |
| CDKN2A | 7 (28.00) | 21 (84.00) | 0.0001 | 7 (31.82) | 1.0000 | 0.0004 |
| CDKN1C | 16 (69.57) | 25 (100.00) | 0.0033 | 10 (43.48) | 0.1362 | <.0001 |
| TP73 | 7 (28.00) | 24 (100.00) | <.0001 | 12 (52.17) | 0.1395 | 0.0001 |
| PAX5 | 12 (46.15) | 23 (92.00) | 0.0006 | 12 (48.00) | 1.0000 | 0.0015 |
| PGK1 | 15 (57.69) | 25 (100.00) | 0.0003 | 19 (76.00) | 0.2367 | 0.0223 |
| PR DIST | 9 (39.13) | 23 (95.83) | <.0001 | 12 (48.00) | 0.5734 | 0.0003 |
| PR PROX | 13 (50.00) | 24 (96.00) | 0.0003 | 8 (33.33) | 0.2650 | <.0001 |
| RARB2 | 8 (32.00) | 24 (96.00) | <.0001 | 9 (39.13) | 0.7640 | <.0001 |
| RB1 | 10 (41.67) | 25 (100.00) | <.0001 | 9 (36.00) | 0.7733 | <.0001 |
| RFC | 15 (57.69) | 25 (100.00) | 0.0003 | 19 (76.00) | 0.2367 | 0.0223 |
| RPL15 | 6 (25.00) | 23 (92.00) | <.0001 | 9 (36.00) | 0.5380 | 0.0001 |
| SOCS1 | 9 (40.91) | 24 (96.00) | 0.0001 | 10 (45.45) | 1.0000 | 0.0002 |
| PRKCDBP | 10 (38.46) | 25 (100.00) | <.0001 | 10 (43.48) | 0.7767 | <.0001 |
| THBS | 14 (56.00) | 24 (96.00) | 0.0019 | 4 (16.00) | 0.0072 | <.0001 |
| TMS1 | 3 (12.00) | 22 (88.00) | <.0001 | 19 (82.61) | <.0001 | 0.6957 |
| TNFSF11 | 6 (25.00) | 21 (100.00) | <.0001 | 13 (54.17) | 0.0753 | 0.0003 |
| VHL | 14 (56.00) | 25 (100.00) | 0.0002 | 9 (37.50) | 0.2563 | <.0001 |

TABLE 3-continued

FREQUENCY OF METHYLATION FOR GENES OF THE
COMPOSITE BIOMARKER FOR BREAST CANCER

|  | Cancer | Normal |
|---|---|---|
| RPL15 | 46% | 87% |
| THBS | 18% | 63% |
| TRANCE | 27% | 70% |
| VHL | 9% | 75% |

TABLE 4

GENES FOR ANALYSIS OF METHYLATION

| Apoptosis | Cell cycle | Signal transduction | Transcription factors | Other |
|---|---|---|---|---|
| DAPK | CYCD2 | ESR1 (A, B) | HIC1 | MDGI |
| RANKL | RB1 | GR | BRCA1 | RIZ |
| APAF1 | p15INK4B | PR (A, B) | SOCS1 | TES |
| TMS1 | p16INK4A | RASSF1A | FHIT | uPA |
| CASP8 | p21WAF1 | EDNRB | PAX5 | MCT1 |
| FAS | p27Kip1 | S100A2 | VHL | HIN1 |
|  | p57Kip2 | SRBC |  | EP300 |
|  | p73 | SYK |  | MUC2 |
|  | SFN |  |  | MCJ |
|  |  |  |  | CALC |

| Angiogenesis | Differentiation | Drug resistance | Invasion | Repair |
|---|---|---|---|---|
| THBS1 | MYOD1 | MDR1 | CDH1 | MLH1 |
|  | RARbeta2 | GSTP | GPC3 | MSH2 |
|  |  | RFC | ICAM1 | MGMT |

TABLE 5 cfpDNA BIOMARKERS CAN DIFFERENTIATE RRMS IN
REMISSION (RMS-R), IN EXACERBATION (RRMS-E), AND
CONTROLS A. Accuracy of Detection

|  | True | |
|---|---|---|
| Predicted | RRMS-R | Healthy Control |
| RRMS-R | 79.2* | 7.1 |
| Healthy Control | 20.8 | 92.9** |

B. Accuracy of Detection

|  | True | |
|---|---|---|
| Predicted | RRMS-E | Healthy Control |
| RRMS-E | 75.9* | 8.5 |
| Healthy Control | 24.1 | 91.5** |

C. Accuracy of Detection

|  | True | |
|---|---|---|
| Predicted | RRMS-E | RRMS-R |
| RRMS-E | 70.8* | 28.8 |
| RRMS-R | 29.2 | 71.2** |

*Sensitivity of biomarker
**Specificity of biomarker
Table 1. cfpDNA biomarkers can differentiate RRMS in remission (RRMS-R), in exacerbation (RRMS-E), and controls.

TABLE 6

DIAGNOSIS OF OVARIAN CANCER
AND BENIGN OVARIAN TUMORS
Table 2. Diagnosis of Ovarian Cancer and
Benign Ovarian Tumors a. Control vs Ovarian Cancer

|  | Predicted | |
|---|---|---|
| True | Control | Cancer |
| Control | 86.9 (74.8-99.0)* | 13.1 |
| Cancer | 20.9 | 79.1 (64.6-93.6)* |

|  | Predicted | |
|---|---|---|
| True | Control | Benign | b. Control vs Benign

| Control | 74.1 (58.4-89.8)* | 25.9 |
| Benign | 21.1 | 78.9 (64.3-93.5)* | c. Ovarian Cancer vs Benign

| Cancer | 71.5 (55.3-87.7)* | 28.6 |
| Benign | 17.7 | 82.3 (68.6-96.0)* |

*95% credible interval

PUBLICATIONS

The following are incorporated by reference to the extent they relate materials and methods of the present disclosure.

Melnikov A A, et al. (2005) MSRE-PCR for analysis of gene-specific DNA methylation Nucleic Acids Res 2005, 33:e93.

Melnikov A A, et al. (2008) Array-based multiplex analysis of DNA methylation in breast cancer tissues. J Mol Diagn, 10:93-101.

The invention claimed is:

1. A method of diagnosing multiple sclerosis (MS) in a subject, the method comprising
  (a) generating a MS methylation profile from a biological sample obtained from the subject, wherein the profile comprises the presence of a plurality of MS biomarker genes; and
  (b) classifying the methylation profile as similar to profiles of patients diagnosed clinically as having MS, to diagnose MS in the subject
wherein the frequency of biomarker methylation is used to classify the profile, and a computer algorithm determines a conditional probability of MS based on the profile.

2. The method of claim 1, applied before a subject has manifested clinical symptoms used to define MS.

3. The method of claim 1, wherein the methylation profile is determined from a plurality of genes listed in Table 1.

4. The method of claim 1, wherein generating a MS methylation profile comprises digesting genomic DNA with a methylation-sensitive enzyme, wherein the enzyme specifically digests unmethylated sites and not hemi-methylated sites.

5. The method of claim 1, wherein the MS biomarker genes are selected from the group consisting of BRCA1, CCND2, DAPK, CDH1, FAS, FHIT, ICAM1, MDG1, MCJ, MUC2, MYF3, CDKN2A, TP73, PAX5, PGK1, PR PROX, RB1, SOCS1 and combinations thereof.

6. The method of claim 4, wherein the enzyme is selected from the group consisting of AciI, HpyCH4IV, Hin6I, HpaII and combinations thereof.

7. The method of claim 1, wherein the conditional probability is $[P_c(g_1/C)*P_c(g_2/C)* \ldots (g_k/C)]$ vs. $[P_c(g_1/nC)*P_c(g_2/nC)* \ldots (g_k/nC)]$, wherein C is MS and nC is non-MS.

8. The method of claim 1, wherein the biomarkers are genomic DNA promotors.

* * * * *